United States Patent [19]

Huber et al.

[11] 4,070,459

[45] Jan. 24, 1978

[54] N-CARBAMYLATED ORGOTEIN

[75] Inventors: Wolfgang Huber, Atherton; Mark G. Saifer, Berkeley; Lewis D. Williams, Menlo Park, all of Calif.

[73] Assignee: Diagnostic Data, Inc., Mountain View, Calif.

[21] Appl. No.: 639,076

[22] Filed: Dec. 9, 1975

[51] Int. Cl.$^2$ .................... A61K 37/14; C07G 7/02; C07G 7/04
[52] U.S. Cl. ................... 424/177; 260/112 R; 260/113; 260/115; 195/68
[58] Field of Search .................. 424/177; 260/112 R, 260/113, 115; 195/68

[56] References Cited

U.S. PATENT DOCUMENTS

| 3,758,682 | 9/1973 | Huber et al. ............... 260/113 X |
| 4,017,605 | 4/1977 | Huber et al. ............... 424/177 |
| 4,022,888 | 5/1977 | Huber et al. ............... 424/177 |

OTHER PUBLICATIONS

Chemical Modification of Proteins, Means & Feeney, pp. 70–71, 74–75, 82, 85, 86–87, 109, 142–143, 146, (1971).

Primary Examiner—Howard E. Schain
Attorney, Agent, or Firm—Millen & White

[57] ABSTRACT

N-carbamylated orgotein, like the native protein, possesses superoxide dismutase and anti-inflammatory activity.

15 Claims, No Drawings

N-CARBAMYLATED ORGOTEIN

BACKGROUND OF THE INVENTION

This invention relates to orgotein derivatives.

Orgotein is the non-proprietary name assigned by the U.S. Adopted Name Council to members of a family of water-soluble protein congeners in substantially pure, injectable form, i.e., substantially free from other proteins which are admixed or associated therewith in the sources thereof. U.S. Pat. No. 3,758,682 claims pharmaceutical compositions comprising orgotein.

The orgotein metalloproteins are members of a family of protein congeners having a characteristic combination of physical, chemical, biological and pharmacodynamic properties. Each of these congeners is characterized physically by being the isolated, substantially pure form of a globular, buffer and water-soluble protein having a highly compact native conformation which, although heat labile, is stable to heating for several minutes at 65° C. at pH 4–10. Chemically, each is characterized by containing all but 0–2 of the protein aminoacids, a small percentage of carbohydrate, no lipids, 0.1 to 1.0% metal content provided by 1 to 5 gram atoms per mole of one or more chelated divalent metals having an ionic radius of 0.60 to 1.00 A., and substantially no chelated monovalent metals or those that are cell poisons in the molecule.

The aminoacid composition of the orgotein congeners is remarkably consistent irrespective of the source from which it is isolated.

Table I lists the distribution of aminoacid residues, calculated for a molecular weight of 32,500 of several orgotein congeners.

SUMMARY OF THE INVENTION

In a composition aspect, this invention relates to N-carbamylated orgotein.

In another composition aspect, this invention relates to pharmaceutical compositions comprising the novel N-carbamylated orgoteins of this invention.

In a method of use aspect, this invention relates to the treatment of inflammatory conditions with a composition of this invention.

DETAILED DISCUSSION

The native orgotein protein possesses uniquely high superoxide dismutase (SOD) activity. See McCord and Fridovich, J. Biol. Chem., 244, 6,049 (1969); Keele, McCord and Fridovich, J. Biol. Chem., 245, 6,176 (1970); ibid., 246, 2,875 (1971). A substantial portion of this activity is retained upon carbamylation of the lysine groups, e.g., 20–100% of the native protein. The anti-inflammatory activity of native protein also is substantially unaffected by carbamylation. Accordingly, the N-carbamylated protein is useful in the same manner as the native protein for the treatment of inflammatory conditions in mammals and other animals as disclosed in U.S. Pat. No. 3,758,682, whose disclosure is incorporated by reference.

As stated above, orgotein congeners contain from 18–26 lysine goups. Since the orgotein molecule is made up of two identical peptide chains (sub-units), half of these lysine groups are in each chain, which are tightly but non-covalently bound together under moderate conditions of temperature and pH. Because of the spacial conformation of the orgotein molecule, usually the $\epsilon$-amino groups of a few lysines in each chain are not

TABLE I

AMINO ACID COMPOSITION OF SEVERAL ORGOTEIN CONGENERS
[Residues per mole, M.W. = 32,500]

| Aminoacids | Liver, Beef | Beef | Sheep | Horse | Pork | Dog | Rabbit | Rat | Guinea Pig | Chicken | Human | Range |
|---|---|---|---|---|---|---|---|---|---|---|---|---|
| Alanine | 19 | 19 | 18 | 18 | 18 | 16 | 19 | 22 | 22 | 23 | 22 | 16–23 |
| Arginine | 8 | 8 | 10 | 6 | 8 | 8 | 8 | 7 | 8 | 8 | 8 | 6–10 |
| Aspartic acid | 37 | 36 | 35 | 35 | 31 | 29 | 34 | 30 | 34 | 36 | 37 | 29–37 |
| Cystine-½ | 6 | 6 | 6 | 6 | 6 | 6 | 6 | 6 | 4 | 10 | 8 | 4–10 |
| Glutamic acid | 21 | 23 | 22 | 30 | 28 | 30 | 25 | 38 | 29 | 26 | 28 | 21–38 |
| Glycine | 53 | 52 | 52 | 51 | 52 | 53 | 54 | 54 | 53 | 56 | 51 | 51–56 |
| Histidine | 16 | 16 | 14 | 20 | 16 | 15 | 17 | 20 | 15 | 17 | 14 | 14–20 |
| Isoleucine | 18 | 18 | 18 | 14 | 16 | 18 | 16 | 16 | 18 | 15 | 17 | 14–18 |
| Leucine | 17 | 17 | 17 | 18 | 16 | 16 | 19 | 12 | 17 | 15 | 20 | 12–20 |
| Lysine | 22 | 21 | 23 | 26 | 23 | 20 | 21 | 18 | 20 | 21 | 23 | 18–26 |
| Methionine | 2 | 2 | 2 | 2 | 2 | 6 | 3 | 4 | 2 | 3 | 1 | 1–6 |
| Phenylalanine | 8 | 8 | 7 | 9 | 8 | 8 | 9 | 6 | 8 | 8 | 8 | 6–9 |
| Proline | 12 | 13 | 15 | 10 | 10 | 10 | 13 | 10 | 12 | 13 | 12 | 10–15 |
| Serine | 17 | 17 | 14 | 14 | 13 | 20 | 18 | 18 | 18 | 15 | 19 | 13–30 |
| Threonine | 26 | 25 | 20 | 16 | 27 | 20 | 21 | 17 | 17 | 18 | 18 | 16–27 |
| Tryptophan[1] | Nil | Nil | Nil | Nil | Nil | Nil | Nil | Nil | Nil | 1 | 2 | 0–2 |
| Tyrosine[2] | 2 | 2 | 2 | Nil | 4 | 2 | Nil | 2 | Nil | 2 | Nil | 0–4 |
| Valine | 33 | 32 | 31 | 29 | 29 | 34 | 31 | 35 | 32 | 30 | 30 | 29–35 |
| Total | 317 | 315 | 306 | 304 | 307 | 311 | 315 | 315 | 309 | 317 | 318 | 304–318 |

[1]Colorimetric determination
[2]Average of amino acid analysis and spectrophotometric determination.

It can be seen from Table I that orgotein congeners have from 18–26 and usually 20–23 lysine groups, of which all but 1–3 have titrable (with trinitrobenzene sulfonic acid) $\epsilon$-amino groups. The present invention is directed to orgotein derivatives in which at least a portion of the orgotein lysine groups are carbamylated.

The term "carbamylated" as used herein embraces both oxo-carbamylated and thio-carbamylated orgoteins, i.e., orgoteins having at least one lysine $\epsilon$-amino group converted to a urea or thiourea group, respectively.

titrable with trinitrobenzenesulfonic acid (TNBS) and thus not readily accessible for carbamylation. However, carbamylation of the non-titrable lysine $\epsilon$-amino groups also appears possible employing a highly active carbamylating agent. The extent of carbamylation can be determined by the decrease in TNBS-reactive amino groups, taking into account that 1–3 of the lysines of the native orgotein protein are not titrable with TNBS. For example, bovine orgotein assays for only 18 of its 20 to 22 lysines.

Carbamylation of the lysine groups can be followed by counting the charge change shown on electrophoresis of the N-carbamylated product. For example, orgotein N-carbamylated with methyl isothiocyanate at pH 9 showed a charge change of −2 after 45 minutes.

As is known, the electrophoretic mobility of an ion is a function of the electric field strength, net charge of the ion (including bound conterions), and frictional coefficient. See, for example, C. Tanford "Physical Chemistry of Macromolecules" Wiley, N.Y. (1966). Since the frictional coefficient is dependent on molecular size and shape, and on the solution composition, comparisons of different proteins are not too informative. However, by comparing proteins of similar size and shape, in this case orgotein molecules chemically modified with relatively small groups, under identical electrophoresis conditions, the only variable affecting this electrophoretic mobility is net charge.

Comparison of the electrophoretic patterns of a number of chemically modified orgotein molecules is consistent with this conclusion. Native bovine orgotein electrophoreses mainly as one band (band 1), with minor amounts of faster moving bands (bands 2,3, etc.) equally spaced ahead of the main band, representing orgotein molecules with a higher ratio of —COOH to —$NH_2$ groups than those molecules forming band 1. Treatment of native bovine orgotein for successively longer periods of time with, e.g., methyl isothiocyanate at pH 9, leads to the formation of a series of successively more anodic (migrating toward the ⊕ electrode) electrophoretic bands as successively more free amino groups of the orgotein molecules are N-carbamylated. Conversely, treatment with dimethyl sulfate gives a series of bands successively more cathodic (displaced from band 1 toward the ⊖ electrode) as successively more free carboxylic acid groups of the orgotein molecule are esterified.

A graph of distance electrophoresed versus band number is relatively linear at low extents of —COOH or —$NH_2$ modification, but curves gradually at higher modification, since there is a limit to how fast even the most highly charged species can move through solution. The faster migrating species are also more sensitive to salt concentration, and are appreciably retarded when salt-containing samples are electrophoresed. Therefore, since extrapolating more than about two band positions is not always precise, accurate charge counting requires that the unknown be co-electrophoresed with a solution which contains all the bands from 1 through the position of interest (e.g., partially N-carbamylated orgotein).

All of the conventional protein modification reactions which have been applied to the orgotein molecule so far have been consistent with this interpretation, viz, the band positions correspond to integral charge changes from the native orgotein molecule. Mild carbamylation and thiocarbamylation both give bands 2, 3, 4, 5, etc., indicating that 1, 2, 3 and 4, respectively, free amino groups have been chemically modified. More extensive carbamylation or thiocarbamylation, which changes even more

gives bands 6, 7, 8, 9, etc. Conversely, esterification, e.g., with dimethyl sulfate or with ethyl diazoacetate, gives bands −1, −2, −3, −4, etc., indicating that 1, 2, 3, and 4, respectively, free carboxylic acid groups have been chemically modified.

Generally speaking, most, e. g., all except 2–4, of the lysines can be readily carbamylated.

As would be expected, when less than all of the titrable lysine amino groups are carbamylated, the distribution of the carbamyl groups on the orgotein molecule probably is random since none of the titrable lysine amino groups appear abnormally readily convertable to carbamylated amino groups. Because the orgotein molecule is composed of two identical peptide chains, the N-carbamylated amino groups of a partially carbamylated orgotein will be distributed more or less randomly along each peptide sub-unit but more or less evenly between the two chains. Since a single carbamylating agent is ordinarily employed, the carbamylated amino groups will all be identical. However, it is possible to produce carbamylated orgoteins having two or more different carbamylated amino groups in the molecule and even within each chain thereof.

One way of producing a mixed N-carbamylated orgotein is by carbamylating in stages with different carbamylating agents. For example, a fraction of the titrable lysine ε-amino groups can be carbamylated with a moderately reactive carbamylating agent, e.g., KNCO, and the remainder of the reactive amino groups alkylated with a more reactive carbamylating agent, e.g., methyl isocyanate. The reactivity of a carbamylating agent depends on the relative rates of reaction with protein amino groups and with the reaction solvent and thus depends on the reaction pH and on the carbamylating agent, and to a lesser extent on buffer and temperature.

Another method of producing a mixed N-carbamylated orgotein is by hybridization. The term hybridization of orgotein refers to the formation of a mixed orgotein from the peptide chains of two different orgotein molecules, e.g., $A_2$ and $B_2$, A and B being their respective peptide chains. ($A_2 + B_2 \rightleftharpoons 2AB$). The charge of the heterodimer, AB, on electrophoresis should be the average of that of the homodimers $A_2$ and $B_2$, assuming that the same portion of each sub-unit is involved in the binding of all cases.

ε-N-propylcarbamyl orgotein, produced by carbamylating the native orgotein molecule in 0.1 M pH 7.6 tris or phosphate buffer with excess propyl isocyanate, and ε-N-methylthiocarbamyl orgotein, produced by carbamylating orgotein in 0.075 M sodium tetraborate with methyl isothiocyanate, can each be hybridized with native orgotein or with each other by heating together at 50° C. for 4 hours.

As will be apparent, these hybrid semi-carbamylated orgotein molecules can be further carbamylated with a different carbamylating agent to produce a hybrid carbamylated orgotein in which the carbamylated amino groups in one peptide chain differ from those in the other.

The ε-N-carbamyl orgoteins of this invention appear to have essentially the same spacial conformation as the native orgotein molecule. Chelated $Cu^{++}$ and $Zn^{++}$ contents (Gram Atoms Per mole) are about the same as that of orgotein. Like orgotein, they are highly resistant to Pronase and other proteolytic enzymatic degradation. Superoxide dismutase (SOD) enzymatic activity is retained, although lessened in proportion to the degree of carbamylation.

Although the predominant structural modification of the native orgotein molecule which occurs upon carbamylation thereof at alkaline pH is the carbamylation of the ε-amino groups of the lysines thereof, the free amino groups of the arginine residues thereof, as well as other alkylatable groups present in the molecule, especially —OH, and imidazole nitrogen, and possibly also guanidino nitrogen, can also be concurrently carbamylated, depending on the conditions employed and the reactivity of the carbamylating agent. However, such concurrently modified groups are labile and readily hydrolyzible in aqueous solutions within a day or less, depending on the pH.

The course of the carbamylation can be followed directly by a change in overall electrophoretic charge, i.e., the disappearance of positive charges, and in the appearance of new bands on electrophoresis at about pH 8.4.

The exact nature of the N-carbamyl groups, like the number thereof, is not critical as long as the carbamyl radical is physiologically acceptable. Because of the higher molecular weight of the orgotein molecule, even when the orgotein molecule is fully carbamylated with carbamyl groups of moderate molecular weight, e.g., $\leq$ 100, the impact of the overall chemical composition is relatively small, i.e., less than 10%. Carbamylation also has no apparent significant effect upon the compact spacial conformation of the molecule and resultant stability, e.g., to heating for 1 hour at 60° C. and to attack by proteolytic enzymes.

As will be apparent, the carbamyl group also must be one derived from a carbamylating agent capable of carbamylating an amino group in water or buffer solution, since the reaction is usually conducted therein. Such carbamylating agents include alkali metal cyanates, e.g., NaNCO, KNCO; alkyl isocyanates and alkyl isothiocyanates, e.g., RNCO and RNCS wherein R = $CH_3$, $C_2H_5$, n-$C_3H_7$, n-$C_4H_9$, n-$C_8H_{17}$; and aryl isocyanates and isothiocyanates, e.g., phenyl isocyanate and phenyl isothiocyanate.

Although metal cyanates react with many types of side chain, only the reaction with amino groups to convert them to urea groups produces a stable product.

The reaction of alkyl isocyanates and isothiocyanates with orgotein is completely analogous to the reaction of cyanates therewith, only much faster. The long chain isocyanates are less reactive than short chain isocyanates.

The reaction of orgotein with isocyanates and isothiocyanates can be confirmed usually by employing a reagent which introduces a fluorescent group into the molecule, e.g., fluorescein isothiocyanate. This reagent is similar to the alkyl isocyanates, and reacts with the amino groups of orgotein to give substituted thioureas. However, even a low level of substitution reduces the SOD activity of orgotein appreciably because of the bulk of the fluorescein. The mono- and disubstituted orgoteins are not stable in solution and slowly become more heterogeneous due to subunit interchange and hydrolysis.

The carbamylated orgoteins of this invention are orgotein congeners, including bovine, sheep, horse, pork, rat, dog, rabbit, guinea pig, chicken and human, at least one, e.g., 1,2,3,4,5 and up to all (about 18-26), of whose titratable amino groups are carbamylated, i.e., bear an unsubstituted or substituted —CONH— or —CSNH— group.

In a preferred embodiment, the carbamylated amino groups are those of the formula

wherein X is O or S and R is $CH_3$, $C_2H_5$, n-$C_3H_7$, iso-$C_3H_7$, n-$C_8H_{17}$ or other alkyl of up to 12 carbon atoms, Ph, or, when X is O, also a hydrogen atom, and Ph is unsubstituted phenyl or phenyl bearing 1-3 simple substituents, e.g., methyl, chloro, bromo, nitro, amido and methoxy, carbomethoxy or carboethoxy, e.g., p-tolyl, sym.-xylyl, p-amidophenyl, m-chlorophenyl and p-methoxyphenyl. Such orgoteins have the formula

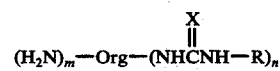

wherein n is an integer from 1 to about 26, preferably at least 2, more preferably about 6 to 10 and the sum of m and n is the total number of titratable free amino groups in the unmodified congener, X is O or S, R has the values given above, preferably H or alkyl of 1-8 carbon atoms, and "Org" is the remainder of the orgotein molecule.

Especially preferred carbamylated orgoteins are alkylcarbamyl and alkylthiocarbamyl orgoteins wherein the alkyl group is unsubstituted alkyl of 1-8 carbon atoms, e.g., methyl, ethyl, propyl, isopropyl, butyl, octyl.

Since the exact chemical nature of the carbamyl group is not critical, so long as it is not physiologically toxic in the orgotein molecule and can be formed on the lysine ε-amino groups, contemplated equivalents of the preferred alkyl carbamyl orgoteins described above, insofar as they can be formed, are those otherwise corresponding to the above formula wherein R is cyclopentyl, cyclohexyl, methyl, and like cycloalkyl, cyclohexylmethyl, β-cyclopentylpropyl, and like cycloalkylalkyl, benzyl, p-xylyl and phenethyl and like aralkyl. Also contemplated as equivalents are those wherein R is alkyl of 1-8, preferably 1-4, and most preferably methyl or ethyl, bearing one or more, preferably one, other substituents, e.g., fluoresceinyl.

In addition to the N-carbamylated "bovine" orgotein of the examples hereinafter, other examples of N-carbamyl bovine orgoteins of this invention are the corresponding N-carbamyl orgotein, N-propylcarbamyl orgotein, N-ethylcarbamyl orgotein, and N-methylthiocarbamyl orgotein wherein in each instance there are 9 such carbamyl groups in each of the two sub-units of the orgotein molecule and the corresponding orgoteins wherein there are an average of 1, 6 or 10 such carbamyl groups in each such sub-unit, respectively, and the corresponding human, sheep, horse, pork, dog, rabbit, guinea pig, chicken and rat congeners of each of these.

The carbamylated orgoteins can be isolated from the reaction solution, preferably after dialysis to remove extraneous ions, by conventional lyophilization, e.g., in the manner described in U.S. Pat. No. 3,758,682. If desired or necessary, the alkylated orgotein can first be purified by ion exchange resin chromatography, electrophoresis and/or gel filtration employing a polymer which acts as a molecular sieve.

Filtration through a micropore filter of pore size 0.01 to 0.22 micron, in an aseptic manner into sterile vials, optionally after adjusting ionic strength with NaCl and/or sodium phosphate, e.g., to isotonicity, will provide a bacterially and virally or bacterially sterile solution suitable for administration by injection. Filtration through a 0.01 micron pore filter will also reduce or eliminate pyrogens in the solution.

The pharmaceutical compositions of this invention comprise an N-carbamyl orgotein of this invention and a pharmaceutically acceptable carrier. The form and character which this carrier takes is, of course, dictated by the mode of administration.

The pharmaceutical composition preferably is in the form of a sterile injectable preparation, for example, as a sterile injectable aqueous solution. The solution can be formulated according to the known art using those carriers most suitable for the route of administration. The sterile injectable preparation can also be a sterile injectable solution or suspension in a non-toxic parenterally acceptable diluent or solvent, e.g., 1, 3-butanediol.

The compositions of this invention combine an effective unit dosage amount of N-carbamylated orgotein, i.e., the N-carbamylated orgotein is present at a concentration effective to evoke the desired response when a unit dose of the composition is administered by the route appropriate for the particular pharmaceutical carrier. For example, liquid compositions, both topical and injectable, usually contain about 0.5 to 20 mg. of N-carbamylated orgotein per 0.25 to 10 cc., preferably about 0.5 to 5 cc., except I.V. infusion solutions, which can also be more dilute, e.g., 0.5 to 20 mg. N-carbamylated orgotein per 50 –1,000 ml., preferably 100–500 ml. of infusion solution. Tablets, capsules and suppositories usually contain 0.1 to 25 mg., preferably 1 to 10 mg., of N-carbamylated orgotein per unit.

N-carbamylated orgotein usually is administered by instillation or by injection, e.g., intramuscularly, subcutaneously, intravenously or intradermally. I.M. is preferred, except in case of shock, where I.V. is sometimes preferred for more rapid onset of effect, and in certain localized disorders, e.g., radiation and intersititial cystitis, where local injection is often more effective. Individual doses usually fall within the range of 0.5 to 20 mg. The preferred range for humans is about 0.5 to 8 mg.; for horses, about 5.0 – 20.0 mg. The exact dosage is not critical and depends on the type and the severity of the disease.

N-carbamylated orgotein, like orgotein, is effective in treating a wide variety of inflammatory conditions, including those in which synthetic anti-inflammatory agents have limited utility, e.g., because of toxic side effects upon prolonged use.

More specifically, N-carbamylated orgotein is efficacious in ameliorating inflammatory conditions and mitigating the effects thereof, for instance, those involving the urinary tract and the joints, in various mammals. It is useful in alleviating the symptoms of and the structural deformities associated with posttraumatic arthritis, and diseases such as bursitis, tendonitis, osteoarthritis and rheumatoid arthritis.

For further details relating to how to isolate the starting orgotein congeners and how to use the N-carbamylated orgotein of this invention, including modes of administration, dosage forms, dosage regimen and inflammatory and other conditions susceptible to treatment with N-carbamylated orgotein, see U.S. Pat. No. 3,758,682.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

Unsubstituted Carbamylated Orgotein

A solution of 3.7 mg. of orgotein (bovine congener) and 14 mg. KNCO in 2 ml. 0.025 M pH 7.5 sodium phosphate buffer was incubated at 4° C. Electrophoresis of aliquot samples over a period of 54 days showed the appearance of a series of SOD active bands more anodic than native orgotein. The average charge change along with the range of active bands on either side of the average for the samples is given below.

Time (days): 0.75, 3.8, 27, 54.
Lysines reacted: 0, 0.8, 5 ± 2, 8.5 ± 3.5.

EXAMPLE 2

Alkyl Carbamylated Orgoteins

50 μl portions of orgotein (bovine congener) in 0.1 M pH 7.6 tris or phosphate buffer at a concentration of 10 mg/ml were reacted at 4° C with either 1 μl of propylisocyanate or octylisocyanate for various times. In two instances, 2 μl additional propyl isocyanate was added after 2 days. The number of propylcarbamyl and octylcarbamyl groups introduced was determined by the average charge change as determined by electrophoresis, as shown below.

| REAGENT | Average Charge Change | | | | + 2 μl isocyanate |
|---|---|---|---|---|---|
| | 2 min. | 2 hr. | 1 day | 2 days | |
| propylisocyanate/tris | 8 | 8 | ND* | ND | 10 |
| propylisocyanate/phosphate | 8 | 8 | ND | ND | >15 |
| octylisocyanate/tris | 0.2 | 1.0 | 6 | 6 | |
| octylisocyanate/phosphate | 0 | 0.2 | 2.5 | 3 | |

*Not done

EXAMPLE 3

Alkyl Carbamylated Orgoteins

The procedure of Example 2 was repeated employing 10 mg. of orgotein in 1 ml 0.1 M pH 7.6 phosphate buffer and 1 ml of propyl or octyl isocyanate. The solutions were maintained at 25° C. for 4 hours and examined electrophoretically. Then an additional 1 ml of the isocyanate was added to each. After incubation at 4° C. overnight, the solutions were again examined electrophoretically and dialyzed. The carbamylated proteins were less soluble in deionized water and partially precipitated on dialysis, but were soluble in 0.15 M saline solution. The number of carbamylated lysine groups are shown below.

| Isocyanate | Lysines Reacted | | GAPM Metal Content | | % of Original SOD Activity |
|---|---|---|---|---|---|
| | 4 Hours | Overnight | Cu++ | ZN++ | |
| propyl | 10±4 | >15 | 2.2 | 1.5 | approx. 50% |
| octyl | 3±3 | 6±5 | 2.1 | 1.8 | approx. 25% |

EXAMPLE 4

N-Methyl Thiocarbamyl Orgotein

To a solution of 5 mg. orgotein in 4 ml. 0.075 M pH 9 $Na_2B_4O_7$ was added 10 μl $CH_3NCS$, and the mixture shaken for a minute until the $CH_3NCS$ dissolved. At intervals, 50 μl samples were withdrawn and quenched with 0.4 ml. 0.1 M pH 5.3 sodium acetate buffer. A white precipitate of sulfur (as shown by its odor on burning and its solubility in $CS_2$) appeared between 6 and 22 hours. After 22 hours at room temperature, the remaining reaction mixture was quenched with 0.5 ml. 1M pH 5.3 acetate buffer and dialyzed vs. frequent changes of water for 2 days. The dialyzed solution was centrifuged briefly to remove the white cloudiness of the solution.

Electrophoresis of samples taken from the solution showed production of a series of increasingly more anodic SOD-active bands. Analysis of the samples by the pH 7.8 cytochrome c assay (McCord & Fridovich, J. Biol. Chem. 6049–6055 (1969)) showed a drop in SOD activity with more extensive modification.

| Time (Hours) | Average Charge Change | SOD Activity % |
|---|---|---|
| 0 | (0) | (100%) |
| 0.08 | 0.5 | 111 |
| 0.25 | 1 | 118 |
| 0.75 | 2 | 91 |
| 1.9 | 4 | 86 |
| 6 | 9.5 | 43 |
| 22 | 16 | 20 |

The dialyzed 22 hour reaction product electrophoresed as a fast-moving anodic band, retained 18% of the SOD activity of the native orgotein protein and contained 2.06 GAPM $Zn^{++}$ and 1.76 GAPM $Cu^{++}$ (compared with 2.26 GAPM Zn and 2.08 GAPM $Cu^{++}$ in unmodified orgotein). All of the products are soluble, retain chelated $Cu^{++}$ and $Zn^{++}$ and at least a portion of the superoxide dismutase activity of the unmodified protein.

EXAMPLE 5

N-Fluoresceinylcarbamyl Orgotein

A solution of 100 mg. orgotein (bovine congener) and 6 mg. fluorescein isothiocyanate in 10 ml. of 0.14 M pH 8.5 phosphate buffer was maintained at 4° C. for 18 hours. The reaction mixture was applied to a chromatographic column of microporous cross-linked dextran (Sephadex G-50, Pharmacia, Upsala, Sweden) and eluted therefrom with pH 8 borate buffered saline (0.15 M). The yellow protein eluted fractions were dialyzed against water. The dialyzed protein which precipitated (20 mg.) was intensely yellow and fluorescent and was readily soluble in pH 8 borate buffered saline. Electrophoresis showed the 96 mg of soluble protein to be about half mono-carbamylated orgotein (−3 charge change) along with some doubly and triply carbamylated orgotein (−6 and −9 charge changes) and unreacted orgotein. The redissolved precipitate appears to be more extensively modified protein, since electrophoresis showed a fast anodic smear.

The soluble protein was chromatographed on a weakly basic (DEAE-cellulose) ion exchange column at pH 6 with 0.01 to 0.2 M linear gradient of phosphate buffer. The mono-carbamylated and the di-carbamylated orgoteins were isolated, dialyzed and lyophylized.

The mono-carbamylated orgotein was SOD active on electrophoresis and NBT-riboflavin staining. According to the pH 7.5 cytochrome c assay, it has 48% of the SOD activity of native orgotein. In the ungar bioassay, that protein showed about 50% of the activity of native orgotein.

A solution of the mono-carbamylated orgotein stored at 4° C. for 2 weeks changed to a mixture of orgotein, monocarbamylated orgotein and dicarbamylated orgotein, (apparently the result of hybridization) and some non-protein fluorescent compound (apparently the result of hydrolysis of the thiourea group of carbamylated orgotein to give free aminofluorescein).

Following the procedure of the above examples but employing, respectively, the corresponding human, sheep, horse, pig, dog, rabbit, guinea pig, rat and chicken orgotein congeners as starting materials, the corresponding carbamylated derivatives of these congeners are produced.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. N-carbamylated orgotein wherein a carbamyl group is present on at least one lysine ε-amino group.
2. A carbamylated orgotein of claim 1, wherein the orgotein is bovine.
3. A carbamylated orgotein of claim 1, having at least two carbamylated ε-amino groups per molecule.
4. A carbamylated orgotein of claim 1, having about 6 to 10 carbamylated ε-amino groups per molecule.
5. A carbamylated orgotein of claim 1, wherein the carbamylated amino group is of the formula

wherein X is O or S and R is alkyl of up to 12 carbon atoms or, when X is O, also a hydrogen atom.

6. A carbamylated orgotein of claim 5, wherein X is O and R is alkyl of 1–8 carbon atoms or a hydrogen atom.
7. A carbamylated orgotein of claim 5, wherein X is S and R is alkyl of 1–8 carbon atoms.
8. A carbamylated orgotein of claim 5, wherein the orgotein is bovine.
9. A carbamylated orgotein of claim 5, having at least two carbamylated ε-amino groups per molecule.
10. A carbamylated orgotein of claim 6, having about 6 to 10 carbamylated ε-amino groups per molecule.
11. A carbamylated orgotein of claim 10, wherein the orgotein is bovine.
12. An alkylated orgotein of claim 7, having about 6 to 10 carbamylated ε-amino groups per molecule.
13. An alkylated orgotein of claim 12, wherein the orgotein is bovine.
14. A pharmaceutical composition comprising, in admixture with a pharmaceutically acceptable carrier, an anti-inflammatorily effective amount per unit dosage of a carbamylated orgotein of claim 1.
15. A method of treating inflammatory conditions in mammals which comprises administering to the affected patient an anti-inflammatorily effective amount of a carbamylated orgotein of claim 1.

* * * * *